(12) United States Patent
Anderson et al.

(10) Patent No.: US 10,346,981 B2
(45) Date of Patent: Jul. 9, 2019

(54) SYSTEM AND METHOD FOR NON-INVASIVE TISSUE CHARACTERIZATION AND CLASSIFICATION

(71) Applicants: Eric Kenneth Anderson, Phoenix, AZ (US); Alana Rae Anderson, Phoenix, AZ (US)

(72) Inventors: Eric Kenneth Anderson, Phoenix, AZ (US); Alana Rae Anderson, Phoenix, AZ (US)

(73) Assignees: Eric Kenneth Anderson, Phoenix; Alana Rae Anderson, Phoenix ( * ) Notice: Subject to any disclaimer, the term of this patent is extended or adjusted under 35 U.S.C. 154(b) by 0 days.

(21) Appl. No.: 15/803,808

(22) Filed: Nov. 5, 2017

(65) Prior Publication Data

US 2018/0130207 A1 May 10, 2018

Related U.S. Application Data

(60) Provisional application No. 62/417,330, filed on Nov. 4, 2016.

(51) Int. Cl.
*G06K 9/00* (2006.01)
*G06T 7/00* (2017.01)
(Continued)

(52) U.S. Cl.
CPC .......... *G06T 7/0014* (2013.01); *A61B 5/055* (2013.01); *A61B 5/7225* (2013.01); *A61B 5/7267* (2013.01); *A61B 6/5217* (2013.01); *A61B 6/5229* (2013.01); *A61B 6/5294* (2013.01); *G06F 16/56* (2019.01); *G06F 19/321* (2013.01); *G06K 9/00147* (2013.01); *G06K 9/6202* (2013.01); *G06K 9/6215* (2013.01); *G06K 9/6256* (2013.01); *G06K 9/6267* (2013.01); *G06T 5/002* (2013.01); *G06T 5/50* (2013.01);
(Continued)

(58) Field of Classification Search
CPC ..... A61B 5/055; A61B 5/7225; A61B 5/7267; A61B 6/032; A61B 6/5217; A61B 5/0022; G06F 19/00; G06F 19/321; G06T 7/0012; G16H 10/60
USPC ............... 382/128, 130, 132, 133, 218, 224; 600/473, 475, 407, 477
See application file for complete search history.

(56) References Cited

U.S. PATENT DOCUMENTS 5,987,346 A * 11/1999 Benaron ............... A61B 5/0059
600/407
8,724,871 B1 * 5/2014 Biagiotti ............... G06T 7/0014
382/128

(Continued)

*Primary Examiner* — Charlotte M Baker
(74) *Attorney, Agent, or Firm* — Barry Choobin; Patent 360 LLC (57) ABSTRACT

The various embodiments herein disclose a system and method for non-invasive computational biopsy analysis. The system is configured to provide diagnosis of human tissue health by non-invasive medical imaging procedures. Further, the system provides a graphical interface providing visual representation of anomalous tissue. The system for computational biopsy includes a Data synthesis module, Signal Filtering module, Classifier module, Analysis Module, Display module, Metric Summary model, Identification of Unknown Tissue module, tissue definition database, and Anomaly Detector module implemented on a computing device.

19 Claims, 5 Drawing Sheets

(51) Int. Cl.
    *G06F 19/00*     (2018.01)
    *G06K 9/62*     (2006.01)
    *G06T 5/50*     (2006.01)
    *G06T 5/00*     (2006.01)
    *A61B 5/055*     (2006.01)
    *A61B 6/00*     (2006.01)
    *A61B 5/00*     (2006.01)
    *G16H 40/63*     (2018.01)
    *G16H 50/30*     (2018.01)
    *G16H 50/20*     (2018.01)
    *G06F 16/56*     (2019.01)
    *A61B 6/03*     (2006.01)
    *G06N 20/00*     (2019.01)

(52) U.S. Cl.
    CPC .......... G06T 7/0012 (2013.01); G16H 40/63 (2018.01); G16H 50/20 (2018.01); G16H 50/30 (2018.01); *A61B 6/032* (2013.01); *G06K 2209/05* (2013.01); *G06N 20/00* (2019.01); *G06T 2200/04* (2013.01); *G06T 2200/24* (2013.01); *G06T 2200/28* (2013.01); *G06T 2207/10088* (2013.01); *G06T 2207/20076* (2013.01); *G06T 2207/20081* (2013.01); *G06T 2207/20084* (2013.01); *G06T 2207/20221* (2013.01); *G06T 2207/30016* (2013.01); *G06T 2207/30096* (2013.01)

(56) References Cited

U.S. PATENT DOCUMENTS

| | | | |
|---|---|---|---|
| 2008/0009748 A1* | 1/2008 | Gratton | A61B 5/0059 |
| 2016/0350946 A1* | 12/2016 | Schieke | G06T 11/008 |
| 2017/0032090 A1* | 2/2017 | Kamen | G06N 7/005 |
| 2017/0200270 A1* | 7/2017 | Reicher | G06F 19/321 |
| 2018/0144828 A1* | 5/2018 | Baker | G16H 15/00 |

* cited by examiner

FIG. 5

SYSTEM AND METHOD FOR NON-INVASIVE TISSUE CHARACTERIZATION AND CLASSIFICATION

CROSS-REFERENCE TO RELATED APPLICATION

The embodiments herein claim the priority of the U.S. Provisional Patent Application with Ser. No. 62/417,330 filed on Nov. 4, 2016, with the title, "A SYSTEM AND METHOD FOR NON-INVASIVE TISSUE CHARACTERIZATION AND CLASSIFICATION", and the contents of which is included entirely as reference herein.

BACKGROUND

Technical Field

The embodiments herein are generally related to a medical diagnostics and biopsy technique. The embodiments herein are particularly related to a non-invasive biopsy of tissues using medical imaging techniques. The embodiments herein are more particularly related to a system and method for non-invasive tissue characterization and classification through computational biopsy.

Description of the Related Art

During a course of medical treatment, there are instances in which the tissues samples must be analyzed. Tissue sample analysis provide an insight into disease or abnormalities in human body. An increasingly important area is the detection and analysis of anatomical regions in the human body. Typically, an invasive surgical biopsy is performed to analyze tissue samples and examine abnormal tissue, lesion, a tumor or a mass. Alternatively, human body is subjected to radiations and Percutaneous needle biopsies to analyze the human body. Aforementioned procedures are invasive, and cause bleeding infection and possibly fatalities.

An improved graphical interface is sought to display a large amount of information. Further, there exists need for a system and method that is non-invasive and prevents radiation exposure to the human body.

The existing tissue sample analysis procedures employ image segmentation. In image segmentation, the user selects markers where gradient-seeking algorithms attempts to reconstruct the image structure. However, image segmentation provides a poor gradient differentiation (i.e. contrast) between tissue types and does not provide accurate results in medical imaging.

Hence, there is a need for a system and method for non-invasive tissue characterization and classification through computational biopsy. Further, there is a need for a system and method for diagnosis of human tissues through non-invasive medical imaging procedures. Still further, there is a need for a system and method for providing visual representation of anomalous tissue through a graphical interface. Yet there is a need for a system and method for in-depth analysis of human tissues without performing biopsy. Yet there is a need for an analytical for diagnosing tissue characterization and classification in a non-invasive manner and without incurring any radiation dose to a patient. Yet there is a need for a system and method for providing an advanced analytics for creating detailed information about the underlying tissue characterization such as cancer, infection, fibrosis, oxygenation, metabolic state, general health, etc.

The above-mentioned shortcomings, disadvantages and problems are addressed herein, which will be understood by reading and studying the following specification.

OBJECTIVES OF THE EMBODIMENTS HEREIN

The primary object of the embodiments herein is to provide a system and method for non-invasive tissue characterization and classification through computational biopsy.

Another object of the embodiments herein is to provide a system and method for generating a computational biopsy.

Yet another object of the embodiments herein is to provide a system and method for diagnosis of human tissue health through non-invasive medical imaging procedures and computational biopsy.

Yet another object of the embodiments herein is to provide a system and method for providing visual representation of anomalous tissue through a graphical interface to medical professional for identifying the targeted biopsy sites.

Yet another object of the embodiments herein is to provide a system and method for in-depth analysis of human tissue without performing invasive surgical biopsy.

Yet another object of the embodiments herein is to provide a system and method for allowing medical professional to identify a targeted biopsy location.

Yet another object of the embodiments herein is to provide a system and method for automatically differentiating between the different types of tissues present in a medical image to assess clinically relevant information such as volume of organs, fraction of healthy tissue in a tissue cluster, areas important to the origin of disease, etc.

Yet another object of the embodiments herein is to provide a system and method for identifying at least one of normal tissue, abnormal tissue, tumors, mass, blood vessels and the like using computational biopsy.

Yet another object of the embodiments herein is to provide a system and method to provide sophisticated visualization and analysis capability to medical professional to summarize the plurality of data in a format comparable to biopsy results.

Yet another object of the embodiments herein is to generate or provide a Machine learning Algorithm to provide a specific identification of normal and abnormal tissue by comparing the results of the Computational Biopsy technique to an internally grown database of observed tissues to enable an analytical tool to label the classification of the medical image or to identify blood vessels, tumors, specific tissue types, etc.

These and other objects and advantages of the embodiments herein will become readily apparent from the following detailed description taken in conjunction with the accompanying drawings.

SUMMARY

The various embodiments herein disclose a system and method system and method for non-invasive tissue characterization and classification through computational biopsy. According to an embodiment herein, the system is configured to provide a diagnosis of human tissue health by analyzing non-invasive medical imaging procedures and generating a computational biopsy. Further, the system provides a graphical interface for providing visual representation of anomalous tissue to medical professional. The system and method thereof provides in-depth analysis of human tissue eliminating the need for a biopsy with a series of standard of imaging procedures. According to an embodiment herein, the system is configured to automatically differentiate between different types of tissues to identify at least one of normal tissue, abnormal tissue, tumors, mass, blood vessels and the like. The system is configured to provide sophisticated visualization and analysis capability to summarize the plurality of data in a format comparable to biopsy results. Thereby, the system enables a doctor/technician to conveniently assess clinically relevant information from the computational biopsy output.

According to an embodiment herein, the system for computational biopsy is provided with a computing system loaded with a Data synthesis module, Signal Filtering module, signal classification module, Analysis Module, and Display module. The computing device is any one of a server device, a client device, and a personal computing device. According to an embodiment herein, the display module is a display device. The system operates on a graphical user interface (GUI) based operating system such as Windows, LINUX, Solaris, and Mac OS.

According to an embodiment herein, the Data synthesis module is configured to collect a plurality of clinically relevant images and laboratory data from various sources. Further, the collected image data is structured to create a set of observation vectors. According to an embodiment herein, the observation vectors include high level objects such as tumor, stroma, necrotic areas, and inflammation are rendered on the graphical user interface (GUI) of the system. Further, low level objects such a nuclei, lumina, and other cell compartments are displayed on the GUI. The data synthesis module is configured to generate a highly accurate multidimensional merge of the plurality of images from different sources.

The data synthesis module is further configured to analyze the merged information for visualization using anomaly detection algorithms. The anomaly data is then fed to the processing module loaded with a processing/visualization algorithm. Anomaly detection algorithms include one of statistical techniques (projection, dimensionality reduction, Mahalanobis based) or machine learning techniques (clustering, classification, etc.).

According to an embodiment herein, the Signal Filtering module is configured to collect merged information. The Signal Filtering module is configured to filter out non-relevant data and ghost image data, thereby providing filtered image outputs. Image filtering is performed by a combination of unsupervised machine learning techniques (clustering, unsupervised neural nets), and supervised machine learning techniques (ensemble methods, decision trees, SVM's, DNN). According to an embodiment herein, the Signal Filtering module is configured to employ image filtering techniques using EM-GMM (expectation maximization for Gaussian mixture models), K-Means, and projection isolation. According to another embodiment herein, the image filtering is performed manually by human classification. In the human classification, visual output of dimensionality reduction techniques/raw images is utilized to select image signals and labels.

The filtered signals from the Signal Filtering module are transferred to the Classifier module. The classifier module compares the filtered signals with database of known samples from an internally developed tissue definition database (TDD for classification. According to an embodiment herein, the classification module is configured to implement statistical metrics. Further, a plurality of machine learning methods (SVM/neural networks) are implemented by the classification module. Alternatively, the filtered signals are sent to an anomaly detector for further analysis.

According to an embodiment herein, the Analysis Module is configured to provide the classified data in layers for visualization and analysis. When new anomalies that are not defined in the TDD are detected by the Analysis Module and are deemed clinically relevant, such anomalies are typically classified as unobserved tumor, infection, normal unobserved tissue. Newly detected anomalies are integrated into the TDD, for future reference for the radiologist and for possible physical biopsy.

Subsequent to processing/visualization by the Analysis Module, a layered 2D or 3D image is output to a user through a graphical interface of the Display module. Each of isolated or removed from the output to allow specific visualization of key anomalies. According to an embodiment herein, the tissue is 3D printed to enable a more accurate model for an actual invasive biopsy.

According to an embodiment herein, a set of Computational Biopsy metrics are provided on the graphical interface of the display module that is further used to indicate a patient health. In an example, this graphical display includes other clinically relevant data such as blood sample results (Triglycerides, HDL and LDL, etc.) are displayed for the doctors. In above example, a new set of indicators is generated to allow the doctor to prescribe remedies. Thus, the system is configured to provide sophisticated visualization and analysis capability to summarize the plurality of data in a format comparable to biopsy results.

According to an embodiment herein, a method for non-invasive computational biopsy is provided. The method involves collecting a plurality of clinically relevant images and laboratory data from various sources by a Data synthesis module. Further, the collected image data is structured to create a set of observation vectors. In an example, the observation vectors includes high-level objects and low-level objects. A highly accurate multidimensional merge of the plurality of images from different sources is generated by the data synthesis module. The merged information is further analyzed for visualization using anomaly detection algorithms. The anomaly data is then fed to a processing/visualization algorithm.

The merged information is collected by the Signal Filtering module. Non-relevant data and ghost image data is filtered from the merged information by the Signal Filtering module, thereby providing filtered image outputs. Image filtering is performed by a combination of unsupervised machine learning techniques (clustering, unsupervised neural nets), and supervised machine learning techniques (ensemble methods, decision trees, SVM's, DNN). Further, the filtered signals from the Signal Filtering module is compared with database of pre-defined samples from an internally developed tissue definition database (TDD) by the classifier module, for classification. Alternatively, the filtered signals are sent to an Anomaly Detection module for further analysis.

The classified data is provided in layers for visualization and analysis by the Analysis Module. When new anomalies that are not defined in the TDD, are detected by the Analysis Module and are deemed clinically relevant, such anomalies are typically classified as unobserved tumor, infection, normal unobserved tissue. Subsequent to processing/visualization by the Analysis Module, a layered 2D or 3D image is output to a user on a graphical interface of the Display module. Each of the tissue element is translated into a 2D or 3D layered image. Each layer in the image is isolated or removed from the output to allow specific visualization of key anomalies. Finally, a set of Computation Biopsy metrics is provided on the graphical interface of the display module that is further used to indicate a patient health.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

BRIEF DESCRIPTION OF THE DRAWINGS

The other objects, features and advantages will occur to those skilled in the art from the following description of the preferred embodiment and the accompanying drawings in which.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS

In the following detailed description, a reference is made to the accompanying drawings that form a part hereof, and in which the specific embodiments that may be practiced is shown by way of illustration. These embodiments are described in sufficient detail to enable those skilled in the art to practice the embodiments and it is to be understood that other changes may be made without departing from the scope of the embodiments. The following detailed description is therefore not to be taken in a limiting sense.

The various embodiments herein disclose a system and method system and method for non-invasive tissue characterization and classification through computational biopsy. According to an embodiment herein, the system is configured to provide a diagnosis of human tissue health by non-invasive medical imaging procedures and computational biopsy. Further, the system provides a graphical interface for providing visual representation of anomalous tissue to medical professional. The system and method thereof provides in-depth analysis of human tissue eliminating the need for a biopsy with a series of standard of imaging procedures. According to an embodiment herein, the system is configured to automatically differentiate between different types of tissues to identify at least one of normal tissue, abnormal tissue, tumors, mass, blood vessels and the like. The system is configured to provide sophisticated visualization and analysis capability to summarize the plurality of data in a format comparable to biopsy results. Thereby, the system enables a doctor/technician to conveniently assess clinically relevant information from the computational biopsy output.

According to an embodiment herein, the system for computational biopsy is provided with a computing system loaded with a Data synthesis module, Signal Filtering module, signal classification ("classifier") module, Analysis Module, Display module, Metric Summary Module, Identification of Unknown Tissue Module, Tissue Definition Database, and Anomaly Detector module. The computing device is any one of a server device, a client device, and a personal computing device. According to an embodiment herein, the display module is a display device (Touch screen, PC display, Virtual Reality device, etc.). The system operates on a graphical user interface (GUI) based operating system such as Windows, LINUX, Solaris, and Mac OS.

According to an embodiment herein, the Data synthesis module is configured to collect a plurality of clinically relevant images and laboratory data from various sources. Further, the collected image data is structured to create a set of observation vectors. According to an embodiment herein, the observation vectors include high-level objects and low-level objects. The data synthesis module is configured to generate a highly accurate multidimensional merge of the plurality of images from different sources.

The data synthesis module is further configured to analyze the merged information for visualization using anomaly detection algorithms. The anomaly data is then fed to the processing module loaded with a processing/visualization algorithm. Anomaly detection algorithms include one of statistical techniques (projection, dimensionality reduction, Mahalanobis based) or machine learning techniques (clustering, classification, etc.).

According to an embodiment herein, the Signal Filtering module is configured to collect merged information. The Signal Filtering module is configured to filter out non-relevant data and ghost image data, thereby providing filtered image outputs. Image filtering is performed by a combination of unsupervised machine learning techniques (clustering, unsupervised neural nets), and supervised machine learning techniques (ensemble methods, decision trees, SVM's, DNN). According to an embodiment herein, the Signal Filtering module is configured to employ image filtering techniques using EM-GMM (expectation maximization for Gaussian mixture models), K-Means, and projection isolation. According to another embodiment herein, the image filtering is performed manually by human classification. In the human classification, visual output of dimensionality reduction techniques/raw images is utilized to select image signals and labels.

The filtered signals from the Signal Filtering module are transferred to the Classifier module. The classifier module compares the filtered signals with database of known samples from an internally developed tissue definition database (TDD for classification. According to an embodiment herein, the classification module is configured to implement statistical metrics. Further, a plurality of machine learning methods (SVM/neural networks) are implemented by the classification module. Alternatively, the filtered signals are sent to an anomaly detector for further analysis.

According to an embodiment herein, the Analysis Module is configured to provide the classified data in layers for visualization and analysis. When new anomalies that are not defined in the TDD are detected by the Analysis Module and are deemed clinically relevant, such anomalies are typically classified as unobserved tumor, infection, normal unobserved tissue. Newly detected anomalies are integrated into the TDD, for future reference for the radiologist and for possible physical biopsy.

Subsequent to processing/visualization by the Analysis Module, a layered 2D or 3D image is output to a user through a graphical interface of the Display module. Each of the tissue element is translated into a 2D or 3D layered image. Each layer in the image is isolated or removed from the output to allow specific visualization of key anomalies. According to an embodiment herein, the tissue is 3D printed to enable a more accurate model for an actual invasive biopsy.

According to an embodiment herein, a set of Computational Biopsy metrics are provided on the graphical interface of the display module that is further used to indicate a patient health. In an example, this graphical display includes other clinically relevant data such as blood sample results (Triglycerides, HDL, and LDL, etc.) are displayed for the doctors. In above example, a new set of indicators is generated to allow the doctor to prescribe remedies. Thus, the system is configured to provide sophisticated visualization and analysis capability to summarize the plurality of data in a format comparable to biopsy results.

According to an embodiment herein, a method for non-invasive computational biopsy is provided. The method involves collecting a plurality of clinically relevant images and laboratory data from various sources by a Data synthesis module. Further, the collected image data is structured to create a set of observation vectors. In an example, the observation vectors includes high-level objects and low-level objects. A highly accurate multidimensional merge of the plurality of images from different sources is generated by the data synthesis module. The merged information is further analyzed for visualization using anomaly detection algorithms. The anomaly data is then fed to a processing/visualization algorithm.

The merged information is collected by the Signal Filtering module. Non-relevant data and ghost image data is filtered from the merged information by the Signal Filtering module, thereby providing filtered image outputs. Image filtering is performed by a combination of unsupervised machine learning techniques (clustering, unsupervised neural nets), and supervised machine learning techniques (ensemble methods, decision trees, SVM's, DNN). Further, the filtered signals from the Signal Filtering module is compared with database of known samples from an internally developed tissue definition database (TDD) by the classifier module, for classification. Alternatively, the filtered signals are sent to an anomaly detector for further analysis.

The classified data is provided in layers for visualization and analysis by the Analysis Module. When new anomalies that are not defined in the TDD, are detected by the Analysis Module and are deemed clinically relevant, such anomalies are typically classified as unobserved tumor, infection, normal unobserved tissue. Subsequent to processing/visualization by the Analysis Module, a layered 2D or 3D image is output to a user on a graphical interface of the Display module. Each of the tissue element is translated into a 2D or 3D layered image. Each layer in the image is isolated or removed from the output to allow specific visualization of key anomalies. Finally, a set of Computation Biopsy metrics is provided on the graphical interface of the display module that is further used to indicate a patient health.

Figure 1:
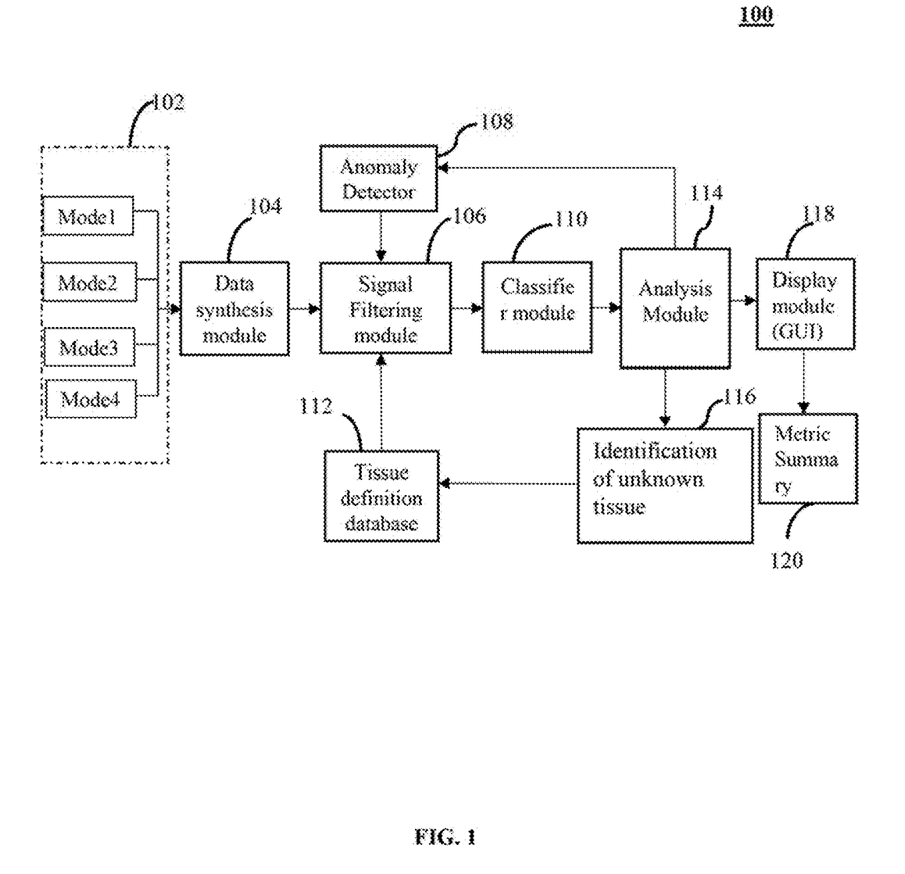
FIG. 1 illustrates a block diagram of a system for non-invasive computational biopsy, according to an embodiment herein.

FIG. 1 illustrates a block diagram of a system for computational biopsy, according to an embodiment herein. The system for computational biopsy has a computing device loaded with a data mode sources 102, Data synthesis module 104, Signal Filtering module 106, Data Classification ("Classifier") module 110, Analysis Module 114, and Display module 118, the Anomaly Detector 108, the Tissue Definition Database 112, the Identification of Unknown Tissue module 116, and the Metric Summary Module 120. The computing device is any one of a server device, a client device, and a personal computing device. According to an embodiment herein, the display module 106 generates the output to display device. The system is operated on a graphical user interface (GUI) based operating system such as Windows, LINUX, Solaris, and Mac OS.

According to an embodiment herein, the data synthesis module is configured to collect a plurality of clinically relevant images and laboratory data from various data sources 102. Further, the collected image data is structured to create a set of observation vectors. In an example, the observation vectors include high-level objects and low-level objects. The data synthesis module is configured to generate a highly accurate multidimensional merge of the plurality of images from different sources.

The data synthesis module is further configured to analyze the merged information for visualization using anomaly detection algorithms 104. The anomaly data is then fed to the processing/visualization algorithm. Anomaly detection algorithms include one of statistical techniques (projection, dimensionality reduction, Mahalanobis based) or machine learning techniques (clustering, classification, etc.).

The Signal Filtering module is configured to collect merged information. The Signal Filtering module is configured to filter out non-relevant data and ghost image data, thereby providing filtered image outputs 106. Image filtering is performed by a combination of unsupervised machine learning techniques (clustering, unsupervised neural nets), and supervised machine learning techniques (ensemble methods, decision trees, SVM's, DNN). According to an embodiment herein, the Signal Filtering module is configured to execute image filtering process using EM-GMM (expectation maximization for Gaussian mixture models), K-Means, and projection isolation. According to an embodiment herein, the image filtering is performed manually by human classification. In the human classification, visual output of dimensionality reduction techniques/raw images is utilized to select image signals and labels.

The filtered signals from the Signal Filtering module are transferred to the Classifier module 110. The classifier module compares the filtered signals with database of known samples from an internally developed tissue definition database (TDD), for classification. According to an embodiment herein, the classification module is configured to deploy statistical metrics. Further, a plurality of machine learning methods (SVM/neural networks) is implemented by the classification module. Alternatively, the filtered signals are sent to an anomaly detector for further analysis.

The Analysis Module is configured to provide the classified data in layers for visualization and analysis 114. When new anomalies that are not defined in the TDD are detected by the Analysis Module and are deemed clinically relevant, such anomalies are typically classified as unobserved tumor, infection, normal unobserved tissue. The newly detected anomalies are integrated into the TDD, for future reference for the radiologist and for possible physical biopsy.

Subsequent to processing/visualization by the Analysis Module, a layered 2D or 3D image is output to a user on a graphical interface of the Display module 118. Each of the tissue element is translated into a 2D or 3D layered image. Each layer in the image is isolated or removed from the output to allow specific visualization of key anomalies. According to an embodiment herein, the tissue is 3D printed to enable a more accurate model for an actual invasive biopsy.

A set of Computation Biopsy metrics is provided on the graphical interface of the display module to indicate a patient health condition 120. In an example, this graphical display includes other clinically relevant data such as blood sample results (Triglycerides, HDL and LDL, etc.) are displayed for the doctors. In above example, a new set of indicators is generated to allow the doctor to prescribe remedies. Thus, the system is configured to provide a sophisticated visualization and analysis capability to summarize the plurality of data in a format comparable to biopsy results.

According to an embodiment herein, object-based image analysis is performed to generate high-level objects and low level objects in the Analysis Module 114. Examples of low-level objects include nuclei, Lumina, cell membrane and cytoplasm. Examples of high-level objects include glands, necrotic areas, tumor regions and epithelial tissue. Further, a number of predefined image features are extracted from each of a plurality of medical images. Based on the predefined features analysis on the plurality of medical images, high level objects such as tumor, stroma, necrotic areas, and inflammation are rendered on the graphical user interface (GUI) of the system. Further, low level objects such a nuclei, lumina, and other cell compartments are displayed on the GUI.

According to an embodiment herein, the Identification of Unknown Tissue module is further configured to generate a multi-dimensional synthesized data set in vector space 116. Thus, the identification of unknown tissue by Signal Filter module is configured to provide an accurate discrimination without any user interaction. Additionally, the Signal Filtering module is configured to enable the user to guide the image analysis through a variety of dimensionality reduction techniques (for example, pca, svd, ICA, pc clustering). Further, accuracy refinements are achieved in image analysis by the addition of patient lab data to the feature vector.

According to an embodiment herein, the images based on multivariate statistics and machine learning are analyzed to assess similarity to the TTD database and further provide tissue classes. Further, multicomponent tissue modalities are identified through a mixture model based approach. The classified data is combined with an internally optimized Expectation Maximization (EM) algorithm to provide an estimate to the amount of 'unknown' tissue that contributes to the classified signal from the Tissue.

Figure 2:
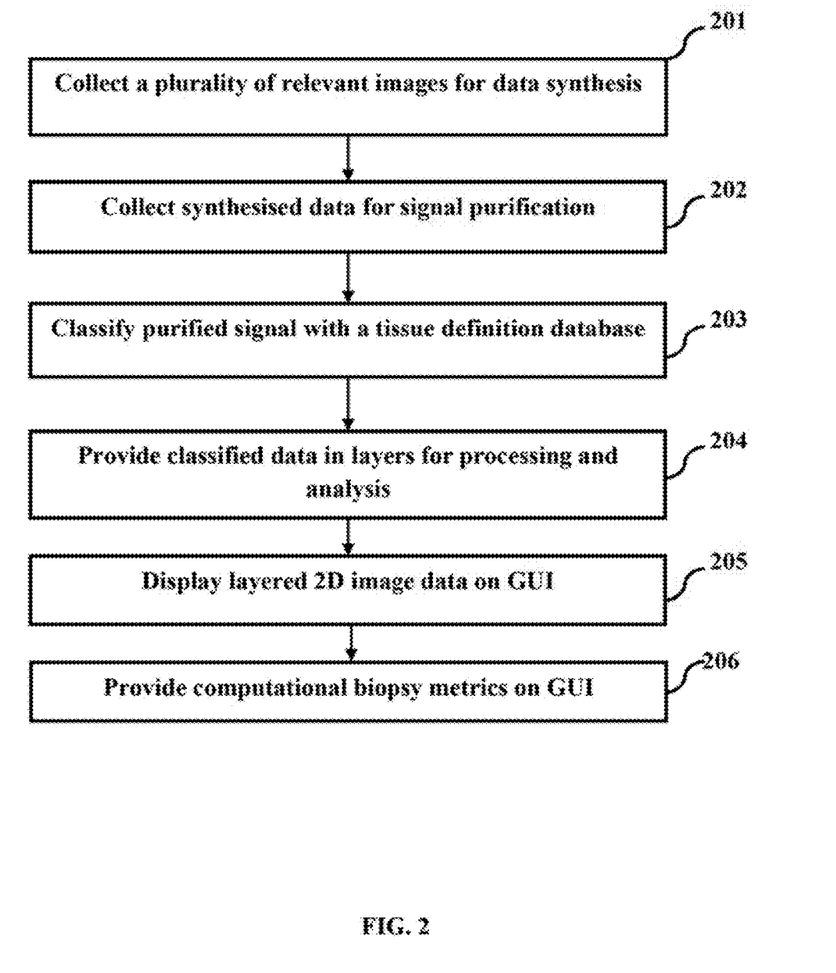
FIG. 2 illustrates a flowchart explaining a method for non-invasive computational biopsy, according to an embodiment herein.

FIG. 2 illustrates a flowchart explaining a method of computational biopsy, according to an embodiment herein. The embodiments herein discloses a computer implemented method comprising computer-readable instructions stored on a non-transitory computer readable medium and executed on a computing device comprising hardware processors (e.g. CPUs and/or GPUs) and a memory, for diagnosing human tissue health by non-invasive medical imaging procedure.

A plurality of clinically relevant images and laboratory data from various sources are collected by a Data synthesis module (201). Further, the collected image data is structured to create a set of observation vectors. In an example, the observation vectors include high-level objects and low-level objects. A highly accurate multidimensional merge of the plurality of images from different sources is generated by the data synthesis module. The merged information is further analyzed for visualization using anomaly detection algorithms. The anomaly data is then fed to a processing/visualization algorithm.

The merged information is collected by the Signal Filtering module (202). Non-relevant data and ghost image data are filtered from the merged information by the Signal Filtering module, thereby providing filtered image outputs. Image filtering is performed by a combination of unsupervised machine learning techniques (clustering, unsupervised neural nets), and supervised machine learning techniques (ensemble methods, decision trees, SVM's, DNN). According to an embodiment herein, the image filtering is performed by the Signal Filtering module using EM-GMM (expectation maximization for Gaussian mixture models), K-Means, and protection isolation.

Further, the filtered signals from the Signal Filtering module is compared with database of known samples from an internally developed tissue definition database (TDD) by the classifier module, for classification (203). Further, a plurality of machine learning methods (SVM/neural networks) is used by the classification module. Alternatively, the filtered signals are sent to an anomaly detector for further analysis.

The classified data is provided in layers for visualization and analysis by the Analysis Module (204). When new anomalies that are not defined in the TDD are detected by the Analysis Module and are deemed clinically relevant, such anomalies are typically classified as unobserved tumor, infection, normal unobserved tissue.

Subsequent to processing/visualization by the Analysis Module, a layered 2D or 3D image is output to a user on a graphical interface of the Display module (205). Each of the tissue element is translated into a 2D or 3D layered image. Each layer in the image is isolated or removed from the output to allow specific visualization of key anomalies.

A set of Computation Biopsy metrics is provided on the graphical interface of the display module that is further used to indicate a patient health condition (206). In an example, this graphical display includes other clinically relevant data such as blood sample results (Triglycerides, HDL and LDL, etc.) are displayed for the doctors. In above example, a new set of indicators is generated to allow the doctor to prescribe remedies. Thus, the method is used to provide sophisticated visualization and analysis capability to summarize the plurality of data in a format comparable to biopsy results.

Figure 3:
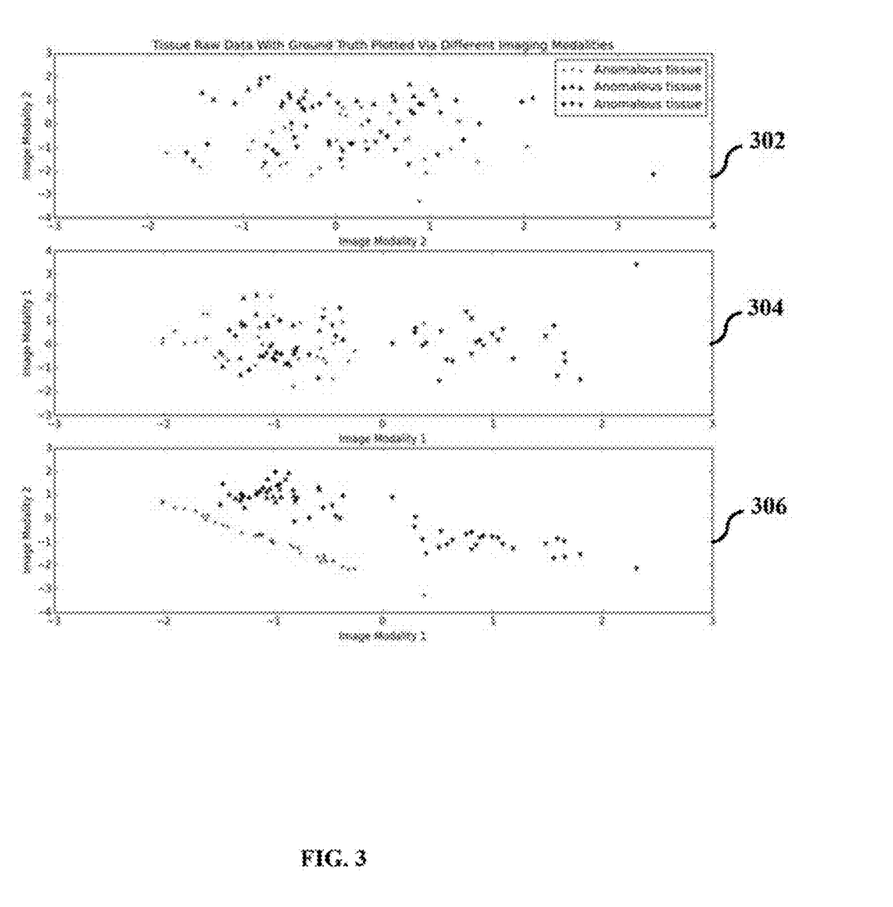
FIG. 3 illustrates a plurality of charts indicating anomalous tissues in a tissue raw data acquired with a plurality of imaging modalities in a method for non-invasive computational biopsy, according to an embodiment herein.

FIG. 3 is an example of the various outputs of the non-invasive tissue classification and characterization system. FIG. 3 displays a first plot with the raw example data plotted from a cluster of approximately 1000 voxels. The first plot 302 displays raw data from the images with wide scattering of data without distinct tissue classification. The second plot 304 displays the output of the non-invasive tissue classification and characterization system after the first stage of data prepossessing. The third plot 306 displays the output of the non-invasive tissue classification and characterization system after signal all the phases of signal filtering are complete. The output after processing the MDD distinctly classifies anomalous tissue. The system generates powerful predictive features from the raw input data and allows for an accurate tissue classification that would have been impossible with the raw MDD.

Figure 4:
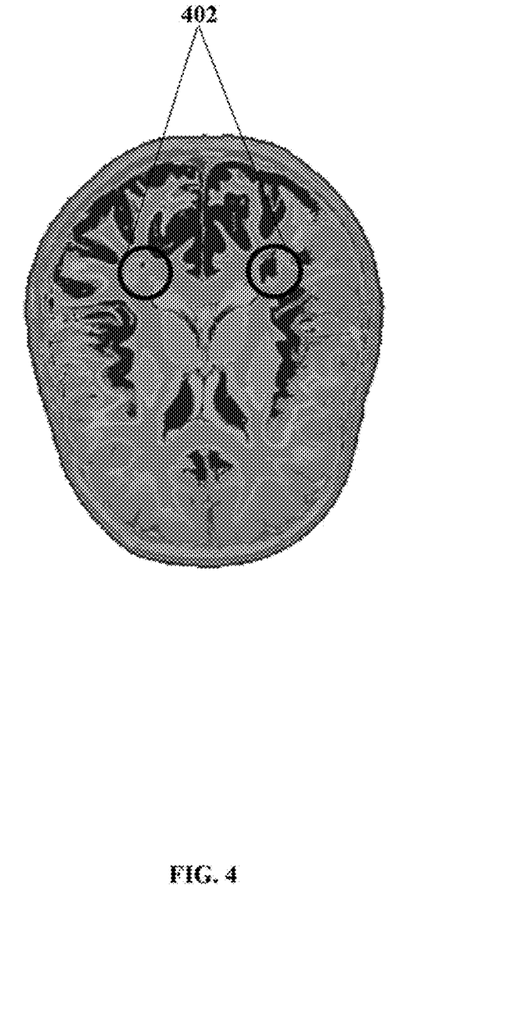
FIG. 4 illustrates an image of a brain scan indicated with anomalies identified using the system for non-invasive computational biopsy for non-invasive tissue classification and characterization, according to an embodiment herein.

FIG. 4 is an example of a 2D brain scan with anomalies identified using the system for non-invasive tissue classification and characterization. With respect to FIG. 4, the output of the human brain from non-invasive tissue classification and characterization system is displayed. The system receives a series of four MRI images as data source. The system analyses the series of images to identify the tissues in human brain as one of normal, healthy, and anomalous tissue. The circled portions in the image 402 indicates the anomalous tissue identified using the system. The system also provide 3D image outputs where each tissue type is presented in layers and are able to be isolated by the physical for better visibility of the anomalies.

Figure 5:
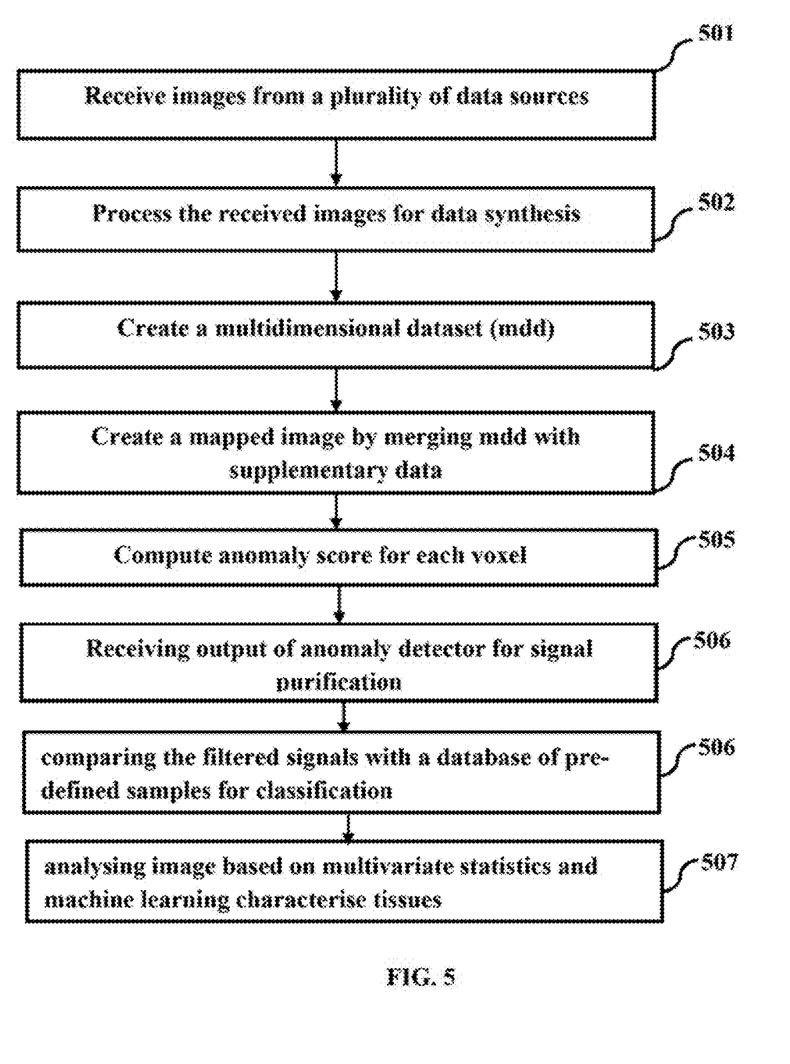
FIG. 5 illustrates a flowchart explaining a process involved in the detection of anomalous tissue from a plurality of images in a method for non-invasive computational biopsy, according to an embodiment herein.

FIG. 5 is a flowchart illustrating the process involved in the detection of anomalous tissue from a plurality of images. According to an embodiment herein, images are received from a plurality of data sources 501. The data sources comprise clinical images, MRI images. The received images are pre-processed for image calibration 502. During image calibration, abnormalities in the image caused by data sources are eliminated. The abnormalities include magnetic b-field artefacts, aliasing, and image bias. Further, the pre-processing includes employing both heuristic methods (for example, selection of isotropic tissue types from across the image) and analytical methods to improve the image quality. After image calibration, the images are co-registered creating a multidimensional dataset (mdd), wherein each pixel of the image is converted into a vector of values 503. The values in the vector correspond to each imaging type included in the analysis. During the creation of each multidimensional dataset, multiple image sources are merging to provide additional exponential detail.

Subsequently, data augmentation is performed by merging data from additional data sources (non-imaging sources) to the mdd, thereby increasing sensitivity 504. The additional data sources include but are not limited to blood test results, family history, hematocrit, computed tomography, and PET. Post data augmentation, image standardization is performed to each mdd by using z-score or demeans image standardization. Image standardization incorporates database values from a database for scaling or using intra-image statistics.

Further, dimensionality reduction is performed using a combination of principle component analysis and manifold learning techniques to create an optimal embedding. Thus, a reduced dimensionality dataset is generated that minimizes or eliminates the effects of degeneracy in the underlying dataset. During image analysis performed to study nature of image data, a degree of degeneracy decreases the analysis accuracy. Thereafter, outlier detection is performed by executing a plurality of anomaly detectors on the merged dataset, thereby generating an anomaly score for each voxel. Examples of the anomaly detectors include but are not limited to classical (pca and Mahalanobis variants), and algorithmic (isolation forest, density isolation methods, support vector machines, and stochastic anomaly seeking neural networks). The anomaly score generated from the merged data is further used to create a list of anomalous voxels 505.

Thereafter, the list of voxels is compared using a similarity metric (of tissues) to map a group of the anomalous voxels into clusters.

According to an embodiment herein, the Signal Filtering module receives the output of the anomaly detector for signal purification. The process of signal purification includes isolating clusters in the dataset to remove noise voxels. The clustering step includes separating voxels into a groups of clusters and individual 'noise' voxels. Thereafter, the noise voxels that degrade analytical accuracy are eliminated from the merged dataset to generate downstream statistical processing data. Further, the group of clusters are tested for statistical power and merged if the statistical power is low. The downstream statistical processing data is fed to the analysis module for data processing and analysis.

According to an embodiment herein, the filtered signals is compared with a database of pre-defined samples for classification by a classifier module 506. The pre-defined samples are retrieved from a tissue definition database (TDD). The images are analyzed based on multivariate statistics and machine learning by the analysis module to characterize tissues 507. The characterization enables visualization of tissue anomalies on a user interface.

Advantageously, the embodiments herein provide a system and method for non-invasive computational biopsy analysis. The system is configured to provide diagnosis of human tissue health by non-invasive medical imaging procedures. Further, the system is configured to provide a graphical interface for projecting a visual representation of anomalous tissue. The system and method thereof provides in-depth analysis of human tissue thereby eliminating the need for biopsy. The system is configured to automatically differentiate between different types of tissues to identify at least one of normal tissue, abnormal tissue, tumors, mass, blood vessels and the like. The system is configured to provide sophisticated visualization and analysis capability to summarize the plurality of data in a format comparable to biopsy results. The invention provides synthesis of a scalable number of data inputs to a clinically relevant computational biopsy output. Thereby, the system enables a doctor/technician to conveniently assess clinically relevant information from the computational biopsy output.

The foregoing description of the specific embodiments will so fully reveal the general nature of the embodiments herein that others can, by applying current knowledge, readily modify and/or adapt for various applications such specific embodiments, without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments, which as a matter of language might be said to fall there between.

What is claimed is:

1. A computer system provided with a hardware processor and a memory loaded with the plurality of algorithms and software applications for non-invasive computational biopsy for tissue classification and characterization using a plurality of algorithms and software applications, the system comprising:
   a data synthesis module, and wherein the data synthesis module is run on the hardware processor and configured to receive images from a plurality of data sources and a laboratory data from a plurality of supplementary data sources, and wherein the plurality of data sources comprises at least one of X-ray scans, clinical images, and MRI images, and wherein the data synthesis module is configured to process the received images for data synthesis, and the data synthesis module is configured to create a multidimensional dataset (MDD), wherein the multidimensional dataset is created by co-registering each voxel of an image with a vector of values, and the data synthesis module is configured to create a mapped image by merging the multidimensional dataset with the plurality of supplementary data sources;
   an anomaly detector run on the hardware processor and configured to create an anomaly score for each voxel of a merged dataset using a plurality of anomaly detection algorithms;
   a Signal Filtering module, and wherein the Signal Filtering module is run on the hardware processor and configured to receive an output from the anomaly detector for signal purification, wherein the Signal Filtering module is configured to generate filtered signals after signal purification;
   a signal classifier module, and wherein the signal classifier module is run on the hardware processor and configured to compare the filtered signals with a plurality of pre-defined samples for classification, wherein the plurality of pre-defined samples are retrieved from a tissue definition database (TDD);
   an Analysis Module, and wherein the Analysis Module is run on the hardware processor and configured to analyze images based on multivariate statistics and machine learning to characterize tissues, to enable visualization of tissue anomalies on a user interface; and
   a display module.

2. The system as claimed in claim 1, wherein the anomaly detector is further configured to:
   generate a list of anomalous voxels for a merged dataset from the anomaly score; and
   map a group of voxels into clusters by comparing the list of anomalous voxels with a similarity metric of tissues.

3. The system as claimed in claim 1, wherein the Signal Filtering module is configured to:
   separate voxels in a merged dataset into a group of clusters and noise voxels; and
   eliminate the noise voxels from the merged dataset to generate statistical processing data, wherein the statistical processing data is fed as a filtered signal to the analysis module.

4. The system as claimed in claim 1, wherein the plurality of supplementary data sources comprises blood test results, family medical history, hematocrit, and computed tomography.

5. The system as claimed in claim 1, wherein the plurality of anomaly detection algorithms include one of statistical techniques (projection, dimensionality reduction, Mahalanobis based techniques) or machine learning techniques (clustering, classification).

6. The system as claimed in claim 1, wherein the Signal Filtering module is configured to filter out non-relevant data and ghost image data, thereby providing filtered image outputs, and wherein the Signal Filtering module is configured to perform an Image filtering process by a combination of unsupervised machine learning techniques (clustering, unsupervised neural nets), and supervised machine learning techniques (ensemble methods, decision trees, SVM's, DNN).

7. The system as claimed in claim 1, wherein, the Signal Filtering module is configured to employ image filtering techniques using EM-GMM (expectation maximization for Gaussian mixture models), K-Means, and projection isolation.

8. The system as claimed in claim 1, wherein the Signal Filtering module is configured to perform an image filtering process manually by a human classification process, and wherein, a visual output of dimensionality reduction techniques/raw images is utilized to select image signals and labels in the human classification-process.

9. The system as claimed in claim 1, wherein the signal classifier module is configured to compare the filtered signals with a database of known samples from an internally developed Tissue Definition Database (TDD) for classification, and wherein the signal classifier module is configured to implement statistical metrics and a plurality of machine learning methods (SVM/neural networks) or the filtered signals are sent to an anomaly detector for further analysis.

10. The system as claimed in claim 1, wherein the Analysis Module is configured to provide a classified data in layers for visualization and analysis, and wherein the Analysis Module is configured to detect new anomalies that are not defined in the TDD and are deemed clinically relevant, and wherein the Analysis Module is configured to classify the new anomalies as unobserved tumor, infection, normal unobserved tissue, and wherein the Analysis Module is configured to integrate the newly detected anomalies into the TDD, for future reference for a radiologist and for possible physical biopsy.

11. The system as claimed in claim 1, wherein a graphical interface of the Display module is configured to output a layered 2D or 3D image to a user after processing/visualization by the Analysis Module, and wherein each of the tissue element is translated into a 2D or 3D layered image, and wherein each layer in the image is isolated or removed from the output to allow specific visualization of key anomalies, and wherein the tissue is 3D printed to enable a more accurate model for an actual invasive biopsy.

12. The system as claimed in claim 1, wherein the graphical interface of the display module is provided with a set of Computational Biopsy metrics to indicate a patient health parameters to allow a doctor to prescribe remedies, and wherein a plurality of clinically relevant patient health parameters are output to the display, and wherein a clinical data includes blood test results (Triglycerides, HDL and LDL).

13. The system as claimed in claim 1, wherein the computer system is any one of a server device, a client device, and a personal computing device.

14. The system as claimed in claim 1, wherein the display module is a display device.

15. A computer implemented method comprising instructions stored on a non-transitory computer readable storage medium and executed on a hardware processor of a computing device comprising processors (e.g. CPUs and/or GPUs) and a memory, for non-invasive tissue classification and characterization using a plurality of algorithms and software applications, the method comprising:

receiving images from a plurality of data sources and a plurality of supplementary data sources with a synthesis module through a software application wherein the plurality of data sources comprises clinical images, CT Scan, MRI images, etc.;

processing the received images by a data synthesis module to create a set of observation vectors, and wherein the set of observation vectors include high level objects and low level objects;

creating a multidimensional dataset (MDD) by the data synthesis module, wherein the multidimensional dataset is created by co-registering each voxel of an image with a vector of values;

creating a mapped image using the data synthesis module by merging the multidimensional dataset with the plurality of supplementary data sources;

computing an anomaly score for each voxel of a merged dataset using anomaly detectors;

receiving an output from an anomaly detector by a Signal Filtering module for signal purification, wherein the Signal Filtering module is configured to generate filtered signals after signal purification;

comparing the filtered signals with a plurality of pre-defined samples for classification by a classifier module, wherein the pre-defined samples are retrieved from a tissue definition database (TDD); and analyzing images based on multivariate statistics and machine learning techniques by an analysis module to characterize tissues, to display tissue anomalies on a user interface.

16. The method as claimed in claim 15, wherein the plurality of supplementary data sources comprise blood test results, family medical history, hematocrit, and computed tomography.

17. The method as claimed in claim 15, wherein the tissues are classified as a tissue known to the TDD or as an anomaly that is not classified yet.

18. The method as claimed in claim 15, wherein the step of executing anomaly detectors to create an anomaly score further comprises:

generating a list of anomalous voxels for a merged dataset from the anomaly score; and mapping a group of voxels into clusters by comparing the list of anomalous voxels with a similarity metric of tissues.

19. The method as claimed in claim 15, wherein the step of signal purification further comprises:

separating voxels in a merged dataset into a group of clusters and noise voxels; and eliminating the noise voxels from the merged dataset to generate statistical processing data, wherein the statistical processing data is fed as a filtered signal to the analysis module.

* * * * *